United States Patent [19]

Huettenrauch et al.

[11] Patent Number: 4,853,948
[45] Date of Patent: Aug. 1, 1989

[54] X-RAY DIAGNOSTICS INSTALLATION FOR OPTIONAL TRANSILLUMINATION OR EXPOSURE OF AN EXAMINATION SUBJECT

[75] Inventors: Gerd Huettenrauch, Uttenreuth; Erhard Jenner, Hessdorf, both of Fed. Rep. of Germany

[73] Assignee: Siemens Aktiengesellschaft, Berlin and Munich, Fed. Rep. of Germany

[21] Appl. No.: 202,816

[22] Filed: Jun. 6, 1988

[30] Foreign Application Priority Data
Jun. 30, 1987 [DE] Fed. Rep. of Germany ....... 3721590

[51] Int. Cl.$^4$ ............................................. G03B 41/18
[52] U.S. Cl. ..................................... 378/177; 378/172; 378/208
[58] Field of Search .............................. 378/172–174, 378/177–179, 181, 182, 208, 209, 205

[56] References Cited

U.S. PATENT DOCUMENTS

| | | |
|---|---|---|
| 3,614,427 | 10/1971 | Vacher ................................ 378/172 |
| 4,417,357 | 11/1983 | Le Sonn ............................. 378/177 |
| 4,667,102 | 5/1987 | Koyama et al. . | |

FOREIGN PATENT DOCUMENTS

| | | |
|---|---|---|
| 1416863 | 10/1968 | Fed. Rep. of Germany . |
| 1939557 | 6/1970 | Fed. Rep. of Germany . |
| 2237272 | 2/1974 | Fed. Rep. of Germany . |
| 2110008 | 5/1972 | France . |
| WO86/06267 | 11/1986 | PCT Int'l Appl. . |

OTHER PUBLICATIONS

Siemens Brochure for "Siregraph C", Oct. 1982.
Siemens Brochure for "Puck", May 1979.

Primary Examiner—Carolyn E. Fields
Assistant Examiner—Joseph A. Hynds
Attorney, Agent, or Firm—Hill, Van Santen, Steadman & Simpson

[57] ABSTRACT

An x-ray diagnostics installation includes an x-ray source, an x-ray image intensifier with a following video chain, a sheet film changer, and a support table for an examination subject. The sheet film changer is mounted on a carriage moveable beneath the patient support table. The x-ray source and the x-ray image intensifier are displaceable together along the support table, and the sheet film changer is positionable by means of the undercarriage in the beam path in front of the x-ray image intensifier, and is couplable thereto so that it follows the movements of the x-ray image intensifier along the support table on its carriage. The installation can thus be optionally used for transillumination or exposure of an examination subject on the table.

11 Claims, 3 Drawing Sheets

X-RAY DIAGNOSTICS INSTALLATION FOR OPTIONAL TRANSILLUMINATION OR EXPOSURE OF AN EXAMINATION SUBJECT

BACKGROUND OF THE INVENTION

1. Field of the Invention

The present invention is directed to an x-ray diagnostics installation operable in a transillumination mode or an exposure mode.

2. Description of the Prior Art

X-ray diagnostics installations are known in the art having components which can be optionally arranged for transillumination or exposure of an examination subject. Such known systems include an x-ray image intensifier with a following video chain, a sheet film changer, an x-ray source and a table or bed for the examination subject. The sheet film changer is mounted on an undercarriage. Such x-ray diagnostics installation offer the possibility of examining the subject in a transillumination mode and, if needed, to produce a direct exposure of a diagnostically relevant area identified in the transillumination mode.

A commercially available x-ray diagnostics installation of this type is the "Puck" system of Siemens-Elema AB, Sweden, as described in Publication No. WS 4788. In this system the x-ray image intensifier is disposed above the patient table on a ceiling mount, and the x-ray source (x-radiator) is disposed in a base of the table. The table has a longitudinally displaceable bearing plate on which the examination subject rests. By means of the carriage on which it is mounted, the sheet film changer can be positioned directly next to the base of the table so that a region of the examination subject, initially transilluminated with the x-ray source and the x-ray image intensifier, can be subsequently positioned in front of the sheet film changer for producing an exposure, by longitudinal displacement of the bearing plate. A second x-ray source disposed on a ceiling mount above the sheet film changer is required for producing this exposure. Apart from the need for two x-ray sources, a disadvantage of this arrangement is that displacement of the examination subject is required in order to change from the transillumination mode to the exposure mode. This is particularly true in the case of angiographic examinations wherein the examination subject is frequently catheterized, or connected to contrast agent injectors, so that displacement of the examination subject cannot be easily undertaken.

The aforementioned Siemens-Elema publication also describes an x-ray diagnostics apparatus wherein only a single x-ray source is required for transillumination and exposure, wherein the x-ray image intensifier and the sheet film changer are arranged side-by-side in the longitudinal direction of the support table in the base thereof beneath the bearing plate. The x-ray source is attached above the bearing plate, and is displaceable together with the bearing plate in the longitudinal direction thereof. To prepare an exposure of a region of the examination subject, which was initially transilluminated, the x-ray source, proceeding from a position in which it is arranged lying opposite the x-ray image intensifier, is displaced together with the bearing plate and the examination subject lying thereon into a position at which the x-ray source lies opposite the sheet film changer. A disadvantage of this system is that the sheet film changer is a fixed component of this system, and thus cannot be used separately. Another disadvantage is that the examination subject again must be shifted in order to change from the transillumination mode to the exposure mode.

A further x-ray diagnostics installation is described in the aforementioned Siemens-Elema publication, wherein the x-ray image intensifier and the x-ray source are attached at opposite ends of an arc-shaped carrier which is height-adjustable, and which can be swivelled in different directions. The sheet film changer is connected to the x-ray image intensifier to form a unit which is pivotable around an axis such that the x-ray image intensifier or the sheet film changer can optionally interact with the x-ray source. This x-ray diagnostic installation permits a simple change to be undertaken from the transillumination mode to the exposure mode, by suitable pivoting of the unit formed of the x-ray image intensifier and the sheet film changer without dislocating the examination subject. A disadvantage of this system, however, is that the arc is stationarily attached in the longitudinal direction of the support table, so that a longitudinal displacement of the bearing plate with the examination subject lying thereon still is required for certain examinations, for example, in the case of angiographic examinations wherein the course of a contrast agent injected into the examination subject is to be observed or recorded in successive regions of the examination subject following each other along the table. Again, the sheet film changer is a fixed component of the system, and cannot be used independently thereof.

SUMMARY OF THE INVENTION

It is an object of the present invention to provide an x-ray diagnostics installation optionally operable in a transillumination mode or an exposure mode, wherein dislocation of the examination subject is not required when changing from one mode to the other, nor when successive regions of an examination subject are to be examined following each other in a direction along the support table.

A further object of the present invention is to provide such an x-ray diagnostics installation wherein only a single x-ray source is required for both transillumination and exposure of an examination subject.

Another object of the present invention is to provide such an installation wherein alignment between the x-ray image intensifier and the x-ray source can be retained in the exposure mode.

Yet another object of the present invention is to provide such an x-ray diagnostics installation wherein the sheet film changer is not a fixed component of the system, and it can be separately employed.

These and other objects are achieved in accordance with the principles of the present invention in an x-ray diagnostics installation wherein the x-ray source and the x-ray image intensifier are mounted to be displaceable in common along the patient support table, and the sheet film changer is positionable beneath the patient support table by means of a carriage on which it is mounted. The sheet film changer is positionable in the beam path in front of the x-ray image intensifier and is couplable thereto such that the carriage on which the sheet film changer is mounted follows movement of the x-ray image intensifier along the patient support. Thus only a single x-ray source is required for both transillumination and exposure of the subject, and alignment of the x-ray source relative to the x-ray image intensifier is not disturbed since the sheet film changer is positionable on its carriage in the beam path in front of the x-ray image intensifier. Moreover, no dislocation the examination subject when changing from the transillumination mode to the exposure mode is needed. Because the x-ray source and the x-ray image intensifier are displaceable in common along the patient support, and the sheet film changer is couplable to the x-ray image intensifier so as to follow the movements thereof along the patient support, the examination subject can remain at rest even when displacement of the x-ray source and the x-ray image intensifier, as well as the sheet film changer, are required during examination. The sheet film changer differs from commercially available sheet film changers mounted on an undercarriage only by the addition of a means for coupling the carriage to the x-ray image intensifier, and thus can be employed independently of the remainder of the x-ray diagnostics installation.

The x-ray image intensifier and the x-ray source in the installation disclosed herein can be attached in a known manner to opposite ends of an arc-shaped carrier which is height-adjustable and pivotable in several directions by means of motorized movement of the carrier under the control of a movement control unit. If this arrangement is used in the present installation, the x-ray image intensifier can be brought to a coupling position for coupling of the sheet film changer, and the movement control unit includes means for blocking all movements of the carrier until coupling of the sheet film changer has been completed, when the sheet film changer is situated in the coupling position in front of the x-ray image intensifier. Movements of the carrier are possible only along the patient support table after completion of coupling of the sheet film changer. This assures that the sheet film changer can be coupled easily to the x-ray image intensifier, and damage to the x-ray image intensifier or the sheet film changer due to unintentional movements of the image intensifier with the sheet film changer positioned in front thereof are avoided. Restricting movements to a direction only along the patient support table after the sheet film changer has been coupled to the image intensifier also serves the same purpose. In order to block other movements in the manner described above, one embodiment of the invention provides first means for interacting with the movement control unit for identifying the presence of the sheet film changer in front o the x-ray image intensifier, and second means interacting with the movement control unit for determining the completion of coupling of the sheet film changer to the x-ray image intensifier.

Generally, the x-ray image intensifier will be situated beneath the patient support table when in the coupling position.

In another embodiment of the invention, the carriage for the sheet film changer has a U-shaped frame surrounding the x-ray image intensifier in the coupling position, and consisting of two horizontal legs and one vertical leg. One of the horizontal legs carries the sheet film changer, and the other horizontal leg is provided with wheels. This structure for the carriage permits the sheet film changer to be easily moved to the x-ray image intensifier, situated in the coupling position, and to couple the sheet film changer thereto.

DESCRIPTION OF THE PREFERRED EMBODIMENTS

Figure 1:
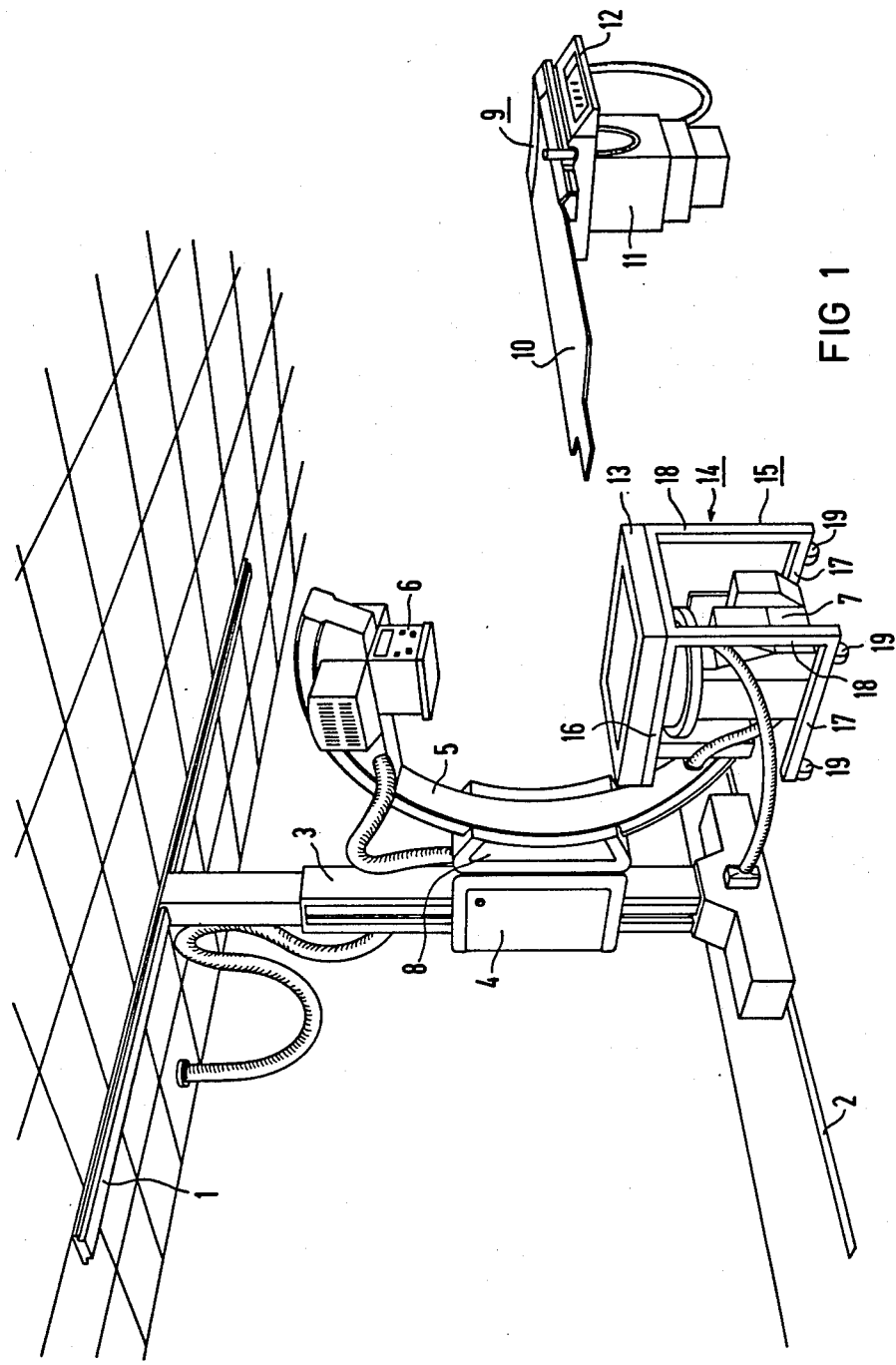
FIG. 1 is a perspective view showing an x-ray diagnostics installation constructed in accordance with the principles of the present invention.

As shown in FIG. 1, an x-ray diagnostics installation constructed in accordance with the principles of the present invention includes a vertical column 3 displaceable along a ceiling rail 1 and a floor rail 2. A carriage 4 is attached to the column 3 in a known manner so as to be height-adjustable. A C-shaped support art 5 is attached thereto, carrying an x-radiator 6 at one end and an x-ray image intensifier 7 at its opposite end. The support arm 5 is adjustable along it circumference in a holder 8 attached to the carriage 4 in a known manner so as to be pivotable around a horizontal axis.

A patient support unit 9 includes a bearing plate 10 which is attached to a base 11. The base 11, and thus the bearing plate 10, are height-adjustable. The ceiling rail 1 and the floor rail 2 proceed parallel to the longitudinal axis of the bearing plate 10, so that the x-radiator 6 and the x-ray image intensifier 7 are displaceable in common along the patient bearing plate 10.

A control panel 12 is attached to the patient support unit 9, the control panel 12 being a component of a control system (not shown) with which movements of the column 3, the carriage 4, the holder 8, the support arm 5 and the bearing plate 10 are controllable by motor drive. With the exception of the blocking function described below, such control of these components proceeds in a manner well-known to those skilled in the art.

The installation also includes a sheet film changer 13, so that an examination subject situated on the bearing plate 10 can be optionally transilluminated using the x-ray image intensifier 7 and a following x-ray video chain (not shown), or can be exposed using the sheet film changer 13. The sheet film changer 13 is mounted on a carriage 14 having a U-shape frame 15 including two upper horizontal legs 15, two lower horizontal legs 17, and two vertical legs 18 connecting the upper and lower horizontal legs. The sheet film changer 13 is attached to the upper horizontal legs 16, and the lower horizontal legs 17 are provided with wheels 19.

For producing exposures, the sheet film changer 13 is positioned by means of the carriage 14 in the beam path in front of the x-ray image intensifier 7 in the position shown in FIG. 1, so that the frame 15 of the carriage 14 surrounds the x-ray image intensifier 7. The sheet film changer 13 is couplable to the x-ray image intensifier 7 in a manner not shown in FIG. 1, but shown in detail in FIG. 2, so that it follows movements of the x-ray image intensifier 7 along the patient bearing plate 10 on the carriage 14. The coupling means provided for that purpose centrally align the sheet film changer 13 relative to the x-radiator 6, and rigidly follow the movements of the x-ray image intensifier 7 along the bearing plate 10. This requires that the coupling means transmit such accelerating forces as may occur.

Figure 2:
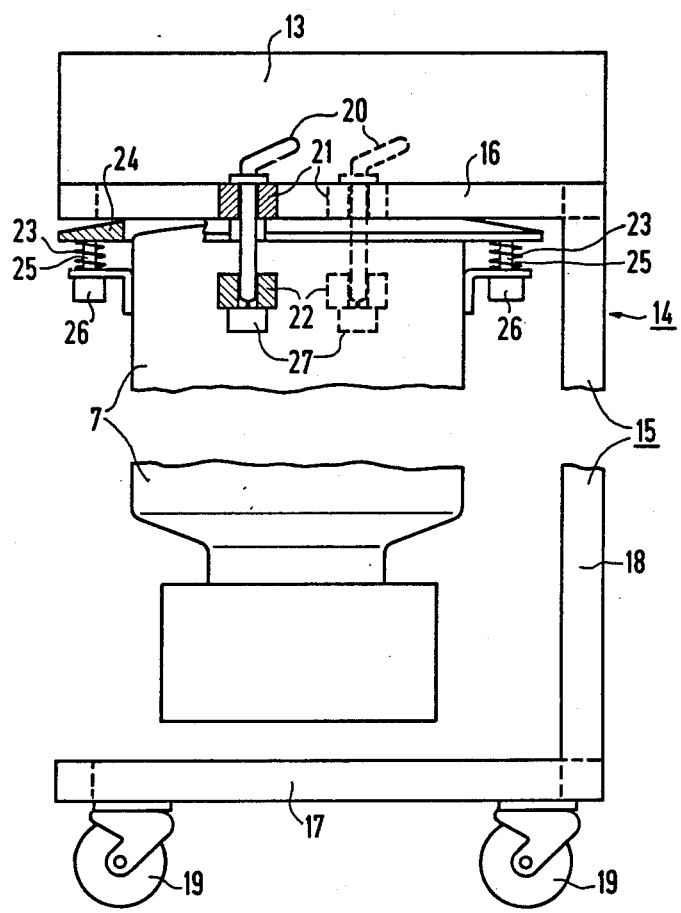
FIG. 2 is a side view, partly in section, of the carriage, and various components mounted thereon, for the x-ray diagnostics installation constructed in accordance with the principles of the present invention.

As long as the x-ray diagnostics installation is being operated in the transillumination mode, the sheet film changer 13 is uncoupled, and is moved to a standby position on the carriage 14, so that it does not impede the attending personnel. When an exposure is to be prepared, the sheet film changer 13 is brought to the installation on the carriage 14, and is coupled to the x-ray image intensifier 7. To facilitate this procedure, the x-ray image intensifier 7 may be moved to a specific coupling position where the sheet film changer 13 is coupled thereto. As can be seen in FIG. 2, the x-ray image intensifier 7 is then situated at a height such that the sheet film changer 13 can just be moved over the x-ray image intensifier 7 by means of the carriage 14. The x-ray image intensifier 7 and the sheet film changer 13 are then coupled to each other by two coupling pins 20 which are longitudinally displaceable in respective guides 21 attached to the upper horizontal legs of the frame 15, and received in the respective bores of two eyelets 22 attached to the x-ray image intensifier 7.

As can also be seen in FIG. 2, a ring 24 resiliently seated on springs 23 is provided at the side of the x-ray image intensifier 7 facing the sheet film changer 13. The ring 24 engages the horizontal legs 16 of the frame 15 and is slightly presses downwardly by the legs 16 in a direction toward the x-ray image intensifier 7 against the action of the springs 23 as soon as one begins to position the sheet film changer 13 in front of the x-ray image intensifier 7. The ring 24 has a plurality of actuators 25 extending downwardly therefrom, which respectively actuate a plurality of switches 26 distributed around the circumference of the x-ray image intensifier 7 as soon as the ring 24 is pressed downwardly. Two additional switches 27 are provided, which are respectively actuated by the coupling pins 20 as soon as those pins are completely introduced into the bores of the respective eyelets 22.

Figure 3:
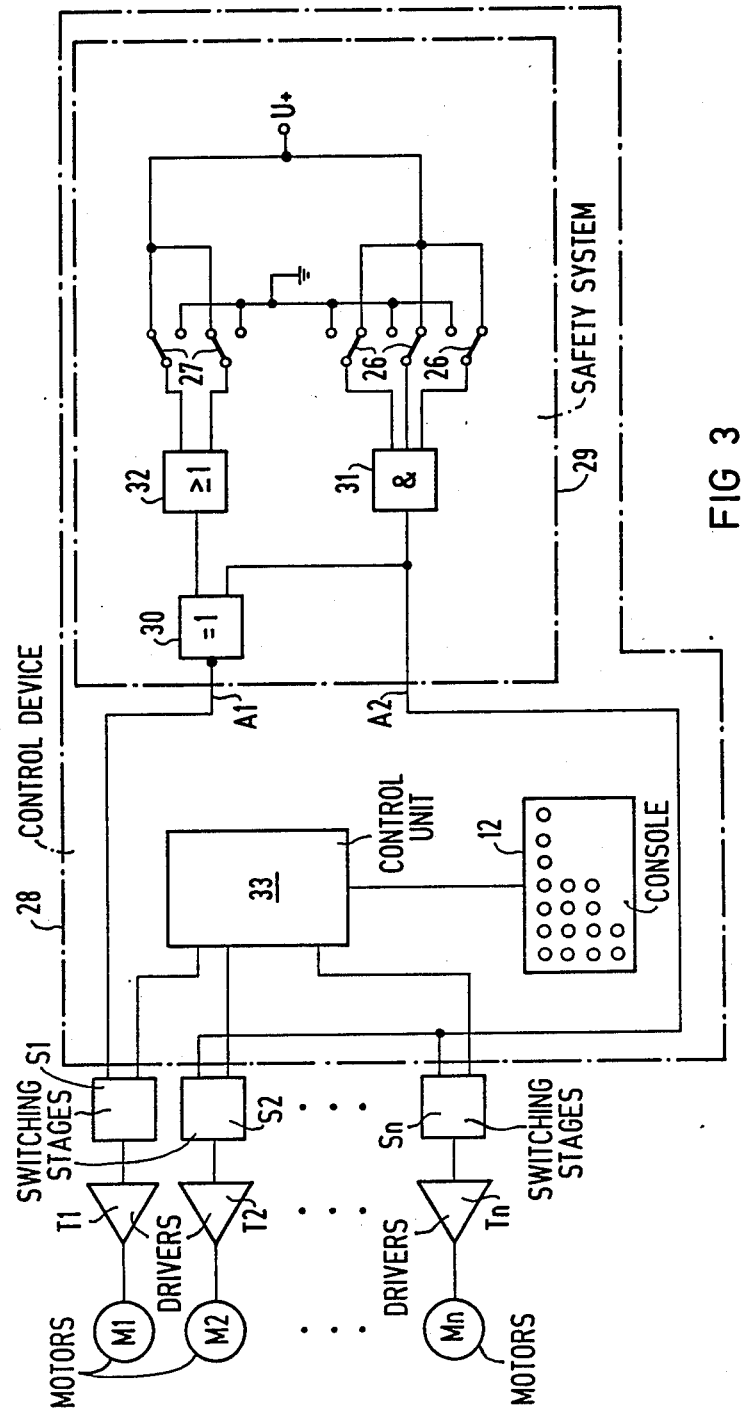
FIG. 3 is a schematic block diagram showing a portion of the relevant control circuitry for the x-ray diagnostics installation disclosed herein.

The ring 24, the springs 23, the actuators 25 and the switches 26 and 27 are parts of a control system, the electrical components of which are schematically shown in FIG. 3.

As shown in FIG. 3, the control system includes a plurality of motors M1, M2 . . . Mn, which effect the aforementioned component movements of the installation. For example, the motor M1 may be used to displace the column 3 along the bearing plate 10. Each of the motors M1 through Mn has a respective driver T1 through Tn allocated thereto. The drivers T1 through Tn are in communication via switching stages S1 through Sn, for example relays, with a control device 28. The control device 28 includes a control unit 33 and the aforementioned control panel 12 connected thereto, so that the individual apparatus movements in the various directions can be produced by suitable actuation of the keys of the control panel 12.

As also shown in FIG. 3, the control device 28 includes a safety system, generally referenced at 29, having two outputs A1 and A2. The output A1 is connected to the switching stage S1, and the output A2 is connected to the remainder of the switching stages S2 through Sn. The safety system 29 also includes the mechanical components described in FIG. 2, the switches 26 (of which three are shown in FIG. 3), the two switches 27, and exclusive NOR gate 30 an AND gate 31, and an OR gate 32. The switches 26 are connected to the inputs of the AND gate 31, and the switches 27 are connected to the inputs of the OR gate 32. Each of the switches 26 and 27 is a double throw switch connected so that the inputs of the AND gate 31 and the inputs of the OR gate 32 can be optionally connected to a positive potential U+(high) or ground potential (low), dependent on the switch position of the switches 26 and 27. The output A2 of the safety system 29 is directly formed by the output of the AND gate 31, and is also connected to one input of the exclusive NOR gate 30. The output A1 of the safety system 29 corresponds to the output of the exclusive NOR gate 30. The other input of the exclusive NOR gate 30 is connected to the output of the OR gate 32.

The operation of the switches 26 and 27 is such that when the sheet film changer 13 is not situated in front of the x-ray image intensifier 7, and consequently is not coupled thereto, all switches 26 and 27 assume a switch position so that the inputs of the AND gate 31 and the inputs of the OR gate 32 (and thus their outputs as well) are high. This means that the output A2 of the safety system 29 as well as the two inputs of the exclusive NOR gate 30, and thus the output A1, are all high. All of the switching stages S1 through Sn are then in a condition which permit control signals of the control device 28 to pass therethrough to the drivers T1 through Tn. Arbitrary apparatus movements can then be effected by the motors M1 through Mn by means of the control panel 12 and the control unit 33.

As soon as the sheet film changer 13 is positioned in front of the x-ray image intensifier 7, at least one of the switches 26 will be actuated via the ring 24 and the corresponding actuator 25, so that the corresponding input of the AND gate 31 will be low. This means that the output of the AND gate 31 will also be low, and thus the output A2 of the safety system 29 will also be low. The output A1 of the safety system 29 will also be low, because different logic levels will now be present at the inputs of the exclusive NOR gate 30. Because both outputs A1 and A2 of the safety system 29 are low, the switching stages S1 through Sn assume a status wherein forwarding of the control signals from the control device 28 to the drivers T1 through Tn is suppressed, so that any and all motor-driven apparatus movement is blocked.

When the sheet film changer 13 positioned in front of the x-ray image intensifier 7 is coupled thereto via the coupling pins 20, the switches 27 are also actuated, resulting in the output of the OR gate 32 becoming low, so that both inputs of the exclusive NOR gate 30 are now low as well. This means that the output A1 of the safety system 29 returns to a high level. This in turn changes the status of the switching stage S1 to permit control signals from the control device 28 to proceed to the driver T1 which, as noted above, effects displacement of the column 3, and thus of the x-radiator 6 and the image intensifier 7 as well as the sheet film changer 13 coupled thereto, along the bearing plate 10 by means of the motor M1. The output A2 of the safety system 29 continues to be at a low level, so that all further apparatus movements continue to be blocked. For the output of the OR gate 32 to become low, it is necessary that the two inputs thereof be low. This means that only motor-drive displacement of the column 3 along the bearing plate 10 is possible when sheet film changer 13 has been correctly coupled to the x-ray image intensifier 7 by the two coupling pins 20.

During uncoupling of the sheet film changer 13 from the x-ray image intensifier 7, all apparatus movements are again blocked in the manner described above. When the sheet film changer 13 is removed completely from the x-ray image intensifier 7, the outputs A1 and A2 of the safety system 29 return to high, so that all apparatus movements are again possible in unrestricted fashion.

The mechanical structure of the coupling means, the control device and the safety system and the carriage for the sheet film changer 13 are provided as an exemplary embodiment, and modifications and changes may be undertaken by those skilled in the art in a manner without departing from the inventive concept disclosed herein.

We claim as our invention:

1. An x-ray diagnostics installation for optional transillumination or exposure of an examination subject comprising:

an x-ray source;

an x-ray image intensifier;

means for supporting a patient between said x-ray source and said x-ray image intensifier;

means for supporting said x-ray source and said x-ray image intensifier and for displacing said x-ray source and said image intensifier in common along said means for supporting a patient;

a sheet film changer;

an independently moveable carriage supporting said sheet film changer having a frame shaped to surround said x-ray image intensifier to permit positioning of said sheet film changer in an x-ray beam path in front of said x-ray image intensifier; and means for coupling said carriage to said x-ray image intensifier so that said carriage and the sheet film changer supported thereon are co-moveable with said x-ray image intensifier and said x-ray source relative to said means for supporting a patient.

2. An x-ray diagnostics installation as claimed in claim 1, further comprising:

means for moving said means for supporting said x-ray source and said x-ray image intensifier in a plurality of directions, including a longitudinal direction relative to said means for supporting a patient, said x-ray image intensifier being moveable by said means for moving to a coupling position;

control means for controlling said means for moving in response to operator-entered commands;

means in said control means for blocking all signals to said means for moving and thereby preventing all movement of said means for supporting said x-ray source and said x-ray image intensifier during coupling of said sheet film changer to said x-ray image intensifier; and means in said control means for restricting movement of said means for supporting said x-ray source and said x-ray image intensifier only to said longitudinal direction as long as said sheet film changer is coupled to said x-ray image intensifier.

3. An x-ray diagnostics installation as claimed in claim 2, wherein said means for blocking includes means for identifying the presence of said sheet film changer in front of said x-ray image intensifier and means for identifying completion of coupling of said sheet film changer to said x-ray image intensifier.

4. An x-ray diagnostics installation as claimed in claim 3, wherein said means for identifying the presence of said sheet film changer in front of said x-ray image intensifier comprises:

a vertically displaceable ring surrounding said x-ray image intensifier at a face thereof adjacent said sheet film changer;

means for normally urging said ring toward said sheet film changer, said sheet film changer moving said ring against said means for urging as said sheet film changer is moved in front of said x-ray image intensifier; and means for generating an electrical signal upon displacement of said ring against said means for urging.

5. An x-ray diagnostics installation as claimed in claim 3, wherein said means for identifying completion of coupling of said sheet film changer to said x-ray image intensifier comprises:

at least one guide carried on said carriage supporting said sheet film changer;

a pin received in said guide;

an eyelet carried on said x-ray image intensifier, said guide and said eyelet being in registry when said sheet film changer is properly positioned relative to said x-ray image intensifier so that said pin extends through both said guide and said eyelet; and means for generating an electrical signal when said pin is received in said eyelet.

6. An x-ray diagnostics installation as claimed in claim 2, wherein said coupling position of said x-ray image intensifier is a position beneath said means for supporting a patient.

7. An x-ray diagnostics installation as claimed in claim 1, wherein said frame of said carriage has a U-shape and comprises a pair of upper horizontal legs carrying said sheet film changer and a pair of lower horizontal legs having wheels thereon, and vertical legs connecting said upper and lower horizontal legs such that said x-ray image intensifier can be received between said upper and lower horizontal legs.

8. An x-ray diagnostics installation as claimed in claim 1, wherein said means for supporting said x-ray source and said x-ray image intensifier is an arc-shaped arm having a first end at which said x-ray source is mounted and an opposite end at which said x-ray image intensifier is mounted.

9. An x-ray diagnostics installation for optional transillumination or exposure of an examination subject comprising:

an x-ray source;

an x-ray image intensifier;

means for supporting a patient between said x-ray source and said x-ray image intensifier;

carrier means supporting said x-ray source and said x-ray image intensifier on opposite sides of said means for supporting a patient;

means for moving said carrier means in a plurality of directions so that said x-ray source and said x-ray image intensifier are moved in common relative to said means for supporting a patient;

control means for operating said means for moving to selectively position said x-ray source and said x-ray image intensifier relative to said means for supporting a patient;

a sheet film changer;

a carriage supporting said sheet film changer which is independently moveable relative to said carrier means, said carriage shaped to surround said x-ray image intensifier to permit positioning of said sheet film changer supported on said carriage in an x-ray beam path in front of said x-ray image intensifier;

means for coupling said sheet film changer to said x-ray image intensifier so that said sheet film changer moves with said x-ray image intensifier as said carrier means is moved;

means in said control means for preventing movement of said carrier means during coupling of said sheet film changer to said x-ray image intensifier; and means in said control means for restricting movement of said carrier means to a longitudinal direction relative to said means for supporting a patient as long as said sheet film changer is coupled to said x-ray image intensifier.

10. An x-ray diagnostics installation as claimed in claim 9, further comprising:

first switch means for generating a signal indicating the presence of said sheet film changer in front of said x-ray image intensifier; and second switch means indicating the completion of coupling of said sheet film changer to said x-ray image intensifier.

11. An x-ray diagnostics installation as claimed in claim 10, further comprising:

a plurality of motors in said means for moving, each motor effecting a different movement of said carrier means, and one of said motors effecting movement of said carrier means in said longitudinal direction;

a plurality of switching stages respectively connected to said plurality of motors, each switching stage having a first state enabling control signals to be transmitted from said control means to the motor associated therewith and a second state preventing said control signals from being transmitted from said control means to the motor associated therewith;

first logic means connected between said first switch means and the switching stages for all of said motors except said one of said motors for placing said switching stages in said second state in the presence of a signal from said second switch means identifying the presence of said sheet film changer in front of said x-ray image intensifier; and second logic means connected to the switching stage of said one of said motors and to said first and second switch means for placing said switching stage in said second state in the presence of a signal from said first switch means indicating the presence of said sheet film changer in front of said x-ray image intensifier and thereafter placing said switching stage in said first state in the presence of a signal identifying the completion of coupling of said sheet film changer to said x-ray image intensifier.

* * * * *